United States Patent [19]

Ehrl et al.

[11] 4,430,272

[45] Feb. 7, 1984

[54] FLUORINE-CONTAINING ALKYLSULFOBETAINES, A PROCESS FOR THEIR PREPARATION AND THEIR USE

[75] Inventors: Winfried Ehrl, Neuötting; Siegfried Jung, Karben, both of Fed. Rep. of Germany

[73] Assignee: Hoechst Aktiengesellschaft, Frankfurt am Main, Fed. Rep. of Germany

[21] Appl. No.: 347,178

[22] Filed: Feb. 9, 1982

[30] Foreign Application Priority Data

Feb. 11, 1981 [DE] Fed. Rep. of Germany ....... 3104766

[51] Int. Cl.³ .............................. C07C 143/14

[52] U.S. Cl. .............................. 260/501.12; 252/8.05; 252/2

[58] Field of Search ...................... 260/501.12, 501.13, 260/501.17

[56] References Cited

U.S. PATENT DOCUMENTS

| | | | |
|---|---|---|---|
| 2,764,602 | 9/1956 | Ahlbrecht | 260/501.13 |
| 3,535,381 | 10/1970 | Hauptscheim et al. | 260/501.17 |
| 3,594,411 | 7/1971 | Kite et al. | 260/501.12 |
| 3,839,425 | 10/1974 | Bartlett | 260/501.12 |
| 4,000,092 | 12/1976 | Wentler | 260/501.12 |
| 4,159,277 | 6/1979 | Grosselink et al. | 260/501.12 |
| 4,283,533 | 8/1981 | Richter | 260/501.12 |

FOREIGN PATENT DOCUMENTS

| | | |
|---|---|---|
| 2749329 | 5/1979 | Fed. Rep. of Germany . |
| 2749330 | 5/1979 | Fed. Rep. of Germany . |

*Primary Examiner*—James H. Reamer

*Attorney, Agent, or Firm*—Curtis, Morris & Safford

[57] ABSTRACT

Fluorine-containing alkylsulfobetaines of the general formula $$R_f-(CF=CH)_a-(CH_2)_b-\overset{\displaystyle R_1}{\underset{\displaystyle R_2}{\overset{|}{\underset{|}{N^+}}}}-(CH_2)_c-SO_3^-,$$

wherein $R_f$ denotes a perfluoroalkyl radical having 3 to 16 C atoms, $R_1$ and $R_2$, which can be identical or different, denote alkyl radicals or hydroxyalkyl radicals having 1 to 4 C atoms, a is zero or 1, b assumes the value 1 when a is equal to 1 and the values 1 to 4 when a is equal to 0, and c is 3 or 4, are described. These are prepared by reacting the corresponding fluorine-containing amines with propanesultone or butanesultone in organic solvents. The compounds are distinguished in particular by high interfacial activity at the interface of water with non-miscible organic liquids and by compatibility with other surfactants. They are suitable for use as aftertreatment agents (auxiliary dispersing agents) in dispersions of fluoropolymers and as components in fire-extinguishing agents.

1 Claim, No Drawings ory, of the compound of Example 1 were obtained. A determination of the amine number showed that the product still contained 0.5% of free amine.

EXAMPLE 3

The procedure of Example 1 was followed, but, instead of ethanol, butylglycol was used as the solvent. 1,715 g of the fluorine-containing amine mentioned in Example 1 and 2,100 g of butylglycol were heated to 60° C. and 425 g of propanesultone were added dropwise at this temperature. The mixture was then stirred for 3 hours at 80° C. 1,000 g of water were then added to produce a 40% strength solution. An amine number determination showed that 0.4% of free amine was still present.

EXAMPLE 4

40 g of (N-1,1,2-trihydro-2-perfluorooctenyl)-N-methylethanolamine, 12 g of propanesultone and 52 ml of butylglycol were reacted according to the procedure of Example 3. The resulting sulfobetaine of the formula

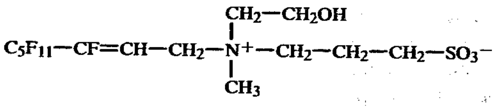

still contained according to the amine number 1.0% of free amine.

EXAMPLE 5

51 g of (N-1,1,2-trihydro-2-perfluorodecenyl)-N-methylethanolamine, 12 g of propanesultone and 63 ml of butylglycol were reacted in accordance with the procedure of Example 3. The resulting sulfobetaine of the formula

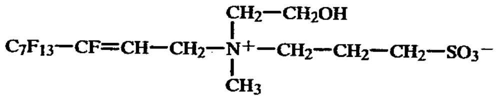

still contained according to the amine number 0.7% of free amine.

EXAMPLE 6

60.5 g of (N-1,1,2-trihydro-2-perfluorododecenyl)-N-methylethanolamine, 12 g of propanesultone and 73 ml of butylglycol were reacted in accordance with the procedure of Example 3. The resulting sulfobetaine of the formula

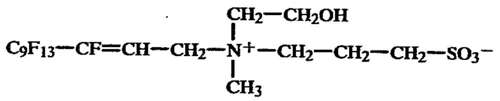

still contained according to the amine number 1.5% of free amine.

EXAMPLE 7

64 g of an (N-1,1,2-trihydro-2-perfluoroalkenyl)-N-dimethylamine (wherein the $R_f$ radical had the meaning mentioned in Example 1), 18.2 g of propanesultone and 83 ml of butylglycol were reacted in accordance with the procedure of Example 3. The resulting sulfobetaine of the formula

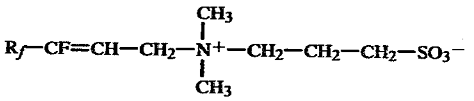

still contained according to the amine number 1.0% of free amine.

EXAMPLE 8

239.5 g of an (N-1,1,2-trihydro-2-perfluoroalkenyl)-N-methylethanolamine (wherein the $R_f$ radical had the meaning mentioned in Example 1) together with 68 g of 1,4-butanesultone and 200 ml of methanol were heated for 4 hours at the boil. After the solvent had been distilled off, a sulfobetaine of the formula

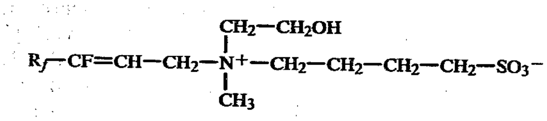

remained as a solid residue and it had an amine number of 2.8. This corresponded to a content of 4% of free amine.

EXAMPLE 9

66 g of an N-1,1,2,2-tetrahydroperfluoroalkyl N,N-dimethylamine of the formula

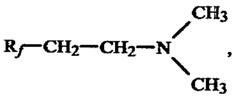 , wherein the radical $R_f$ had the following composition:

41% by weight of $C_6F_{13}$-,
40% by weight of $C_8F_{17}$-,
14% by weight of $C_{10}F_{21}$- and
5% by weight of $C_{12}F_{25}$-, and 18.2 g of propanesultone were reacted in 83 ml of butylglycol in accordance with the procedure of Example 3. The resulting sulfobetaine of the formula

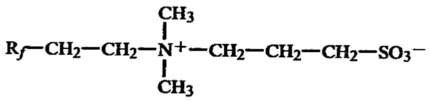

still contained according to the amine number 1.5% of free amine.

The structure of the sulfobetaines obtained was confirmed by $^1H$—NMR spectra and IR spectra thereof.

The table below shows the superior properties of aqueous solutions of sulfobetaines according to the invention in respect to their surface tension and their interfacial surface tension towards cyclohexane in comparison to fluorine-containing sulfatobetaines and two commercial products recognized as good, which are also fluoro surfactants and contain quaternary ammonium groups:

FLUORINE-CONTAINING ALKYLSULFOBETAINES, A PROCESS FOR THEIR PREPARATION AND THEIR USE

The invention relates to fluorine-containing alkylsulfobetaines, a process for their preparation and their use.

The new compounds have the general formula

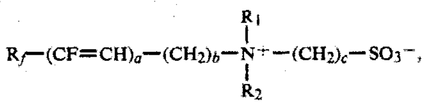

wherein $R_f$ denotes a perfluoroalkyl radical having 3 to 16 C atoms, $R_1$ and $R_2$, which can be identical or different, denote alkyl radicals or hydroxyalkyl radicals having 1 to 4 C atoms, a is zero or 1, b assumes the value 1 when a is equal to 1 and the values 1 to 4 when a is equal to 0, and c is 3 or 4.

Preferably $R_1$ and $R_2$, identical or different, denote in these compounds an alkyl radical or a hydroxyalkyl radical having 1 to 2 C atoms and a denotes the value 1.

The present invention also relates to a process for the preparation of the fluorine-containing alkylsulfobetaines defined above, which comprises reacting a fluorine-containing amine of the general formula

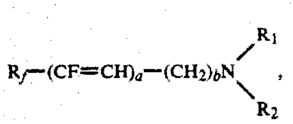

wherein $R_f$, $R_1$, $R_2$, a and b have the meaning defined above, with a sultone of the general formula

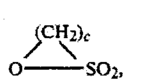

wherein c has the meaning defined above, in an organic solvent.

The fluorinated amines used as a starting compound are known and they can be prepared, for example by methods described in U.S. Pat. No. 3,257,407, U.S. Pat. No. 3,535,381, German Auslegeschrift No. 1,668,794, German Offenlegungsschrift No. 1,768,939 or German Offenlegungsschrift No. 2,141,542. Propanesultone or butanesultone serves as a sulfoalkylating agent. The reaction is carried out in an organic solvent which must be inert to the reactants. Examples of solvents which are suitable for the reaction are methanol, ethanol, butylglycol, butyldiglycol or acetone. The reaction temperature is advantageously in the range from 50° to 100° C. and the reaction is carried out under virtually unpressurized conditions. At these temperatures the sulfoalkylation takes between 1 and 10 hours. The sultones are advantageously not used in excess of the stoichiometrically required amount since they are toxic. At the end of the sulfoalkylation the fluorinated alkylsulfobetaines can be obtained in a solid form by distilling off the solvent. However, for many end uses the solution of the products in an organic solvent which results from the sulfoalkylation can also be used. The sulfoalkylation can also be carried out with mixtures of fluorinated amines (a denoting zero or 1).

Fluorine-containing alkylsulfobetaines, according to the invention, of the formula defined above are distinguished by a considerable lowering of the surface tension (water/air) and in particular by a high interfacial activity at the interface of water with non-miscible organic liquids, especially hydrocarbons. The fluorinated alkylsulfatobetaines disclosed in German Offenlegungsschrift No. 2,749,329 only produce such a lowering of the interfacial surface tension of water/non-miscible organic liquid at the low application concentrations used in practice if a secondary component with a synergistic action, such as, for example, a fluorinated alkylammonium monoalkyl-sulfate, described in German Offenlegungsschrift No. 2,749,330, is present. However, such quaternary ammonium salts are not compatible with anionic surfactants which may be present, for example, in fire-extinguishing agents, whilst fluorinated alkylsulfobetaines according to the invention are perfectly compatible with cationic, non-ionic and anionic surfactants. Finally, fluorine-containing alkylsulfobetaines according to the invention are also far superior to known fluorine-containing alkylsulfatobetaines with regard to their resistance to hydrolysis.

Fluorine-containing alkylsulfobetaines according to the invention are suitable because of their high compatibility with other non-ionic surfactants, such as, for example, oxyalkylated phenols, for use as a post-added dispersion stabilizer in the manufacture of polytetrafluoroethylene dispersions and dispersions of other fluoropolymers or fluorocopolymers, also suitable for use as a flow control agent in waxes, as a dry-cleaning detergent in dry cleaning and, in particular because of their high interfacial activity, as components in fire-extinguishing agents.

The examples below are intended to illustrate the invention in greater detail.

EXAMPLE 1

245 g of an (N-1,1,2-trihydro-2-perfluoroalkenyl)-N-methylethanolamine, the perfluorinated alkyl radical $R_f$ of which was composed of a mixture of various perfluorinated alkyls which had the following composition:

41% by weight of $C_5F_{11}$-,
40% by weight of $C_7F_{15}$-,
14% by weight of $C_9F_{19}$- and
5% by weight of $C_{11}F_{23}$-, were dissolved in 300 ml of ethanol, and 60 g of propanesultone were added dropwise with stirring at 70° C. The mixture was then boiled under reflux for 3 hours, and thereafter the solvent was distilled off. The product was slurried in acetone and the precipitated solid was filtered off. This isolated 210 g of a product of the formula

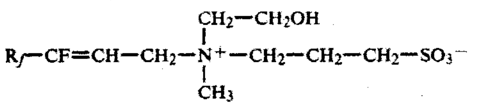

which corresponded to a yield of 69% of theory. An amine number determination produced the value 0.

EXAMPLE 2

The procedure of Example 1 was followed, but acetone was used instead of ethanol. After filtering and drying, 298 g, corresponding to a yield of 97% of the-

TABLE

| Surfactant | Surface tension in water[3] mN/m 0.1 g/l | 0.03 g/l | Water/ cyclohexane 0.1 g/l | interfacial surface tension[3] mN/m 0.03 g/l |
|---|---|---|---|---|
| Sulfobetaine of Example 3 | 23.0 | 28.5 | 16.8 | 24.2 |
| Sulfobetaine of Example 4 | 37.5 | 46.2 | 25.0 | 34.2 |
| Sulfobetaine of Example 5 | 22.0 | 26.5 | 13.7 | 19.5 |
| Sulfobetaine of Example 6 | 29.5 | 30.0 | 15.5 | 23.0 |
| Comparative Experiments: | | | | |
| Sulfatobetaine from German Offenlegungsschrift 2,749,329, Example 4 | 57.9 | 61.8 | 48.1 | 49.6 |
| Sulfatobetaine from German Offenlegungsschrift 2,749,329, Example 1 | 19.1 | 20.1 | 41.7 | 43.3 |
| Forafac ® 1095[1] | 46.0 | 56.0 | 30.1 | 40.2 |
| Zonyl ® FSC[2] | 45.1 | 59.7 | 28.5 | 36.7 |

[1]Commercial product from Messrs. Ugine Kuhlmann
[2]Commercial product from Messrs. Du Pon
[3]Measured by means of a Du Noey tensiometer

We claim:

1. A fluorine-containing alkylsulfobetaine of the general formula $$R_f\text{—}(CF{=}CH)_a\text{—}(CH_2)_b\text{—}\overset{\displaystyle R_1}{\underset{\displaystyle R_2}{N^+}}\text{—}(CH_2)_c\text{—}SO_3^-,$$

wherein $R_f$ denotes a perfluoroalkyl radical having 3 to 16 C atoms, $R_1$ and $R_2$, which can be identical or different, denote alkyl radicals or hydroxyalkyl radicals having 1 to 4 C atoms, a is zero or 1, b assumes the value 1 when a is equal to 1 and the values 1 to 4 when a is equal to 0, and c is 3 or 4.

* * * * *